(12) United States Patent
Van Der Poel et al.

(10) Patent No.: US 11,612,324 B2
(45) Date of Patent: *Mar. 28, 2023

(54) DERIVING TOOTH CONDITION INFORMATION FOR POPULATING DIGITAL DENTAL CHARTS

(71) Applicant: 3SHAPE A/S, Copenhagen K (DK)

(72) Inventors: Mike Van Der Poel, Rødovre (DK); Rune Fisker, Virum (DK); Karl-Josef Hollenbeck, Copenhagen Ø (DK)

(73) Assignee: 3SHAPE A/S, Copenhagen K (DK)

( * ) Notice: Subject to any disclaimer, the term of this patent is extended or adjusted under 35 U.S.C. 154(b) by 172 days.

This patent is subject to a terminal disclaimer.

(21) Appl. No.: 17/128,273

(22) Filed: Dec. 21, 2020

(65) Prior Publication Data

US 2021/0106229 A1 Apr. 15, 2021

Related U.S. Application Data

(63) Continuation of application No. 15/780,519, filed as application No. PCT/EP2016/079749 on Dec. 5, 2016, now Pat. No. 10,902,595.

(30) Foreign Application Priority Data

Dec. 4, 2015 (DK) .............................. PA201570803

(51) Int. Cl.
*G06K 9/00* (2022.01)
*A61B 5/00* (2006.01)
(Continued)

(52) U.S. Cl.
CPC .......... *A61B 5/0062* (2013.01); *A61B 5/0088* (2013.01); *A61B 5/1032* (2013.01);
(Continued)

(58) Field of Classification Search
CPC .................. G06T 7/0014; G06T 7/12; G06T 2207/30036; G06T 2207/10028;
(Continued)

(56) References Cited

U.S. PATENT DOCUMENTS 5,356,294 A 10/1994 Odomo
6,102,704 A * 8/2000 Eibofner .............. A61B 5/7475
433/29
(Continued)

FOREIGN PATENT DOCUMENTS

CN 1536977 A 10/2004
CN 101579263 A 11/2009
(Continued)

OTHER PUBLICATIONS

Office Action issued in corresponding Japanese Patent Application No. 2018-528286, dated Jan. 4, 2022, with English Translation (4 pages).

(Continued)

*Primary Examiner* — Van D Huynh
(74) *Attorney, Agent, or Firm* — Buchanan Ingersoll & Rooney PC (57) ABSTRACT

Disclosed are methods and digital tools for deriving tooth condition information for a patient's teeth, for populating a digital dental chart with derived tooth condition information, and for generating an electronic data record containing such information.

20 Claims, 6 Drawing Sheets

(51) Int. Cl.
| | |
|---|---|
| *A61C 9/00* | (2006.01) |
| *G16H 50/20* | (2018.01) |
| *G16H 10/60* | (2018.01) |
| *A61B 6/14* | (2006.01) |
| *G06T 7/12* | (2017.01) |
| *G16H 30/40* | (2018.01) |
| *A61B 5/103* | (2006.01) |
| *G06T 7/00* | (2017.01) |
| *A61C 13/00* | (2006.01) |
| *G16H 30/20* | (2018.01) |
| *G06T 7/32* | (2017.01) |
| *G06T 7/70* | (2017.01) |
| *G06T 3/00* | (2006.01) |

(52) U.S. Cl.
CPC .......... *A61B 5/4547* (2013.01); *A61B 6/145* (2013.01); *A61C 9/0046* (2013.01); *G06T 7/0014* (2013.01); *G06T 7/12* (2017.01); *G16H 10/60* (2018.01); *G16H 30/40* (2018.01); *G16H 50/20* (2018.01); *A61B 5/0066* (2013.01); *A61B 5/0071* (2013.01); *A61B 5/7475* (2013.01); *A61C 13/0004* (2013.01); *G06T 3/0068* (2013.01); *G06T 7/32* (2017.01); *G06T 7/70* (2017.01); *G06T 2207/10028* (2013.01); *G06T 2207/30036* (2013.01); *G16H 30/20* (2018.01)

(58) Field of Classification Search
CPC .......... G06T 3/0068; G06T 7/70; G06T 7/32; A61B 5/4547; A61B 5/0062; A61B 6/145; A61B 5/1032; A61B 5/0088; A61B 5/7475; A61B 5/0066; A61B 5/0071; G16H 10/60; G16H 30/40; G16H 50/20; G06F 19/321; A61C 9/0046; A61C 13/0004
USPC ......................................................... 382/128
See application file for complete search history.

(56) References Cited

U.S. PATENT DOCUMENTS

| | | | | |
|---|---|---|---|---|
| 7,341,450 | B2* | 3/2008 | Pye ........................ | A61C 19/10 356/402 |
| 7,596,253 | B2* | 9/2009 | Wong .................. | A61B 5/0088 382/128 |
| 8,013,853 | B1 | 9/2011 | Douglas et al. | |
| 8,416,984 | B2* | 4/2013 | Liang .................. | G16H 10/60 382/154 |
| 9,158,889 | B2 | 10/2015 | Badawi | |
| 2002/0178032 | A1* | 11/2002 | Benn ...................... | G16H 10/60 705/2 |
| 2004/0029068 | A1 | 2/2004 | Sachdeva et al. | |
| 2005/0089214 | A1 | 4/2005 | Rubbert et al. | |
| 2006/0069591 | A1 | 3/2006 | Razzano | |
| 2007/0168152 | A1* | 7/2007 | Matov .................... | G16H 30/20 702/155 |
| 2009/0274998 | A1* | 11/2009 | Wong .................. | A61B 5/0088 433/215 |
| 2010/0121658 | A1* | 5/2010 | Kaminski .............. | A61C 19/00 715/790 |
| 2011/0045428 | A1 | 2/2011 | Bultunov et al. | |
| 2012/0189182 | A1* | 7/2012 | Liang .................... | A61C 19/00 382/128 |
| 2014/0037180 | A1 | 2/2014 | Wang et al. | |
| 2014/0172375 | A1 | 6/2014 | Grove et al. | |
| 2015/0294066 | A1 | 10/2015 | Golay | |
| 2015/0320320 | A1* | 11/2015 | Kopelman ............. | G06T 7/344 433/215 |
| 2018/0357766 | A1 | 12/2018 | Van Der Poel et al. | |

FOREIGN PATENT DOCUMENTS

| | | |
|---|---|---|
| EP | 2479694 A2 | 7/2012 |
| EP | 2 639 764 A1 | 9/2013 |
| JP | 2012150801 A | 8/2012 |
| JP | 2013-192939 A | 9/2013 |

OTHER PUBLICATIONS

Office Action issued in corresponding Brazilian Patent Application No. BR112018011227-5, dated Mar. 12, 2021 (6 pages) and translation thereof.
Office Action issued in corresponding Japanese Patent Application No. 2018-528286, dated Jun. 15, 2021 (7 pages) and translation thereof.
Office Action issued in corresponding European Patent Application No. 16 805 469.0-1126, dated Feb. 8, 2021 (5 pages).
International Search Report (PCT/ISA/210) dated Feb. 24, 2017, by the European Patent Office as the International Searching Authority for International Application No. PCT/EP2016/079749.
Written Opinion (PCT/ISA/237) dated Feb. 24, 2017, by the European Patent Office as the International Searching Authority for International Application No. PCT/EP2016/079749.
First Office Action issued in corresponding Chinese Patent Application No. 2016800800042, dated Mar. 21, 2020, with English Translation (17 pages).
Preliminary Office Action dated Mar. 25, 2020, by the Brazilian Patent Office in corresponding Brazilian Patent Application No. BR112018011227-5, and a partial English Translation of the Office Action (5 pages).
Second Office Action dated Sep. 14, 2020, by the Chinese Patent Office in corresponding Chinese Patent Application No. 2016800800042, and an English Translation of the Office Action (12 pages).
Office Action (Notice of Reasons for Rejection) dated Oct. 6, 2020, by the Japanese Patent Office in corresponding Japanese Patent Application No. 2018-528286, and an English Translation of the Office Action (5 pages).
Report of Pretrial Examination issued in Japanese Trial No. 2022-006494 (Japanese Patent Application No. 2018-528286), dated Sep. 5, 2022, with English Translation (5 pages).

* cited by examiner

DERIVING TOOTH CONDITION INFORMATION FOR POPULATING DIGITAL DENTAL CHARTS

The present application is a continuation of U.S. patent application Ser. No. 15/780,519, which was filed on May 31, 2018, which is a national stage application of PCT/EP2016/079749, which was filed on Dec. 5, 2016, and which claims the priority of Danish Patent Application No. PA 201570803, which was filed on Dec. 4, 2015. The subject matter of U.S. Ser. No. 15/780,519; PCT/EP2016/079749; and Danish Patent Application No. PA 201570803 is incorporated herein by reference.

TECHNICAL FIELD

This invention generally relates to methods, systems, computer program products and digital environments for deriving tooth condition information for a patient's teeth and for populating dental charts with tooth condition information. More particularly, the invention relates to methods, systems, computer program products and digital environments where individual teeth are identified from a digital 3D representation of the patient's teeth and the derived tooth condition information is correlated with the individual teeth.

BACKGROUND

Dental practice management systems frequently use dental charts for storing information regarding a patient's dental situation. Such dental charts are known as an efficient tool for visualizing information regarding the condition of a patient's teeth.

Standardized dental charts often has regions representing the surfaces of the individual teeth normally found in a patient's mouth. In such charts there is usually one specific region for each specific tooth surface. Different colors, geometrical figures or other visual representations are used to visualize e.g. caries, dental restorative work, root problems etc. on the dental chart.

Digital dental charts are also know e.g. from U.S. Pat. No. 8,416,984 wherein a method for generating a digital dental chart from a scan of the patient's teeth and populating the generated digital dental chart with tooth condition information is disclosed.

In prior art systems derived tooth condition information is manually annotated/mapped/transferred onto the standardized/schematic representation of the patient's teeth used in the dental practice management systems. This is both time consuming and is prone to human error risking that e.g. the information is annotated to the wrong part of the tooth or even to the wrong tooth.

It remains to provide method and digital tools for deriving tooth condition information for a patient's teeth and for populating a digital dental chart with such information which have fewer manual steps and accordingly are less prone to human errors. The digital tools can e.g. be a computer system, a computer program product, or a digital environment.

SUMMARY

Disclosed is a Method for Deriving Tooth Condition Information for a Patient's Teeth,
wherein the method comprises:
obtaining a digital 3D representation of the patient's teeth;
identifying the individual teeth in the digital 3D representation;
segmenting the individual teeth from the digital 3D representation;
obtaining diagnostic data for one or more of the teeth;
deriving tooth condition information from the diagnostic data; and
correlating the derived tooth condition information with the individual teeth.

The segmentation and identification of the teeth in the digital 3D representation provides that it is known which portions of the digital 3D representation relate to the patient's individual teeth. The arrangement of the individual teeth in the digital 3D representation is thus also known.

When the spatial correlation between the diagnostic data and the digital 3D representation also is known the segmentation and identification of the teeth in the digital 3D representation provides that the diagnostic data can be correlated with the individual teeth. i.e. it can be determined for which tooth the diagnostic data are recorded from. The spatial correlation between the diagnostic data and the digital 3D representation is known e.g. when the diagnostic data are comprised in the digital 3D representation or when the spatial correlation is determined by aligning parts of the diagnostic data with corresponding parts of the digital 3D representation.

When the diagnostic data are spatially correlated with the digital 3D representation the spatial correlation between the individual teeth of the digital 3D representation and the tooth condition information derived from the diagnostic data will then often also be known. Accordingly, the segmentation and identification of the teeth provides that the derived tooth information can be linked to the patient's individual teeth, i.e. it can be determined for which tooth a given tooth condition information is derived for.

In some embodiments, correlating the derived tooth information with the identified and segmented teeth comprises determining the location of the tooth condition on the tooth. The tooth condition information can then be mapped onto the correct position on the region of the dental chart.

As explained above, tooth condition information can be visualized in a digital dental chart. Accordingly herein is also disclosed a method for populating a digital dental chart with tooth condition information, wherein the method comprises:
deriving tooth condition information for one or more of the teeth by using the method, system, computer program product and/or digital environment according to any of the embodiments;
obtaining a digital dental chart comprising regions representing surfaces of the patient's teeth;
correlating the individual teeth with the corresponding regions of the digital dental chart; and
adding a representation of the derived tooth condition information to the corresponding region or regions of the digital dental chart.

I.e. the method, the computer program product, the digital environment, and the system may be configured for populating a digital dental chart with tooth condition information for the individual teeth of a patient.

A standardized digital dental chart often has regions representing the surfaces of the individual teeth normally found in a patient's mouth. In such charts there is usually one specific region for each specific tooth surface. The segmentation and identification of the individual teeth in a digital 3D representation provides that the teeth portions of the digital 3D representation can be linked to the corresponding regions of the digital dental chart. The knowledge of the spatial correlation between the digital 3D representation and the diagnostic data provides that it is known which tooth the derived tooth condition information relates to. The representation of the derived tooth condition information can thus be added to the correct region of the dental chart representing the tooth surface for which the tooth condition information was derived for.

When the derived tooth condition information is added to a digital dental chart the digital dental chart expresses the current condition of least one tooth with respect to at least one dental condition such as the presence of e.g. caries, cracks in the tooth surface or dental restorations.

In some cases the digital dental chart is populated and visualized in a dental practice management system. Herein is also disclosed a method for generating an electronic data record configured for use in a dental practice management system, where the electronic data record comprises tooth condition information for the individual teeth of a patient, wherein the method comprises:
  deriving tooth condition information for one or more of the teeth by using the method, system, computer program product and/or digital environment according to any of the embodiments; and
  storing the tooth condition information for the identified teeth in the electronic data record.

Disclosed is a Method Comprising:
  obtaining a digital 3D representation of a patient's teeth;
  obtaining diagnostic data for one or more of the teeth;
  identifying individual teeth of the digital 3D representation;
  deriving tooth condition information from the diagnostic data, and
  correlating the derived tooth information with the identified individual teeth.

Disclosed is a digital environment configured for assisting an operator in performing the steps of the disclosed method.

Disclosed is a computer program product comprising computer readable instructions which when executed by an electronic data processing device provides a digital environment for performing the steps of the disclosed method.

Disclosed is a System Comprising:
  an electronic data processing device; and
  a non-transitory computer readable medium encoded with the disclosed computer program product.

In some embodiments, the method, the computer program product, the digital environment, or the system is for deriving tooth condition information for the individual teeth of a patient.

In some embodiments, the method, the computer program product, the digital environment, or the system is for populating a digital dental chart with tooth condition information for the individual teeth of a patient. The method then comprises a step of populating the digital dental chart with the derived tooth condition information.

In some embodiments, the method, the computer program product, the digital environment, or the system is for generating an electronic data record configured for use in a dental practice management system, where the electronic data record comprises tooth condition information for the individual teeth of a patient. The method then comprises storing the derived tooth condition information for the identified teeth in the electronic data record.

In some embodiments, the method comprises segmenting individual teeth from the digital 3D representation.

The segmentation and identification of the individual teeth in a digital 3D representation provides that the teeth portions of the digital 3D representation can be linked to the corresponding regions of the digital dental chart. This provides for a more efficient and faster procedure which is less prone to human errors.

Disclosed is a Digital Environment Comprising:
  a digital loading tool for loading a digital 3D representation of the patient's teeth and diagnostic data for one or more of the teeth into the digital environment;
  a digital work space adapted for visualizing the digital 3D representation and/or the diagnostic data;
  a digital identification tool for identifying individual teeth of the digital 3D representation;
  a digital deriving tool for deriving tooth condition information from the diagnostic data, and
  a digital correlating tool for correlating the derived tooth information with the identified individual teeth.

In some embodiments, the digital environment comprises a digital segmentation tool for segmenting the individual teeth from the digital 3D representation.

In some embodiments, the digital environment comprises a digital populating tool for populating a digital dental chart with the derived tooth condition information. Disclosed is a Digital Environment Comprising a Digital Work Space, where the Digital Environment is Configured for:
  obtaining a digital 3D representation of the patient's teeth and displaying the digital 3D representation in the digital work space;
  obtaining diagnostic data for one or more of the teeth; and
  assisting an operator in performing the steps of a method comprising:
    identifying individual teeth in the digital 3D representation;
    segmenting the individual teeth from the digital 3D representation;
    deriving tooth condition information from the diagnostic data; and
    correlating the derived tooth information with the individual teeth.

Disclosed is a User Interface Configured for Deriving Tooth Condition Information for a Patient's Teeth, wherein the User Interface is Configured for:
  obtaining a digital 3D representation of the patient's teeth;
  identifying individual teeth in the digital 3D representation;
  segmenting the individual teeth from the digital 3D representation;
  obtaining diagnostic data for one or more of the teeth;
  deriving tooth condition information from the diagnostic data; and
  correlating the derived tooth information with the individual teeth.

Disclosed is a system for deriving tooth condition information for a patient's teeth, wherein the system is configured for obtaining a digital 3D representation of the patient's teeth and diagnostic data for one or more of the teeth, and where the system comprises a non-transitory computer readable medium encoded with a computer program product comprising computer readable instructions for:
  identifying individual teeth in the digital 3D representation;
  segmenting the individual teeth from the digital 3D representation;
  deriving tooth condition information from the diagnostic data; and
  correlating the derived tooth information with the individual teeth.

Disclosed is a System for Deriving Tooth Condition Information for a Patient's Teeth, the System Comprising:
an electronic data processing device; and
a non-transitory computer readable medium encoded with
a computer program product comprising computer readable instructions which when executed by the electronic data processing device provides a digital environment for deriving tooth condition information for the teeth by a method comprising:
i. obtaining a digital 3D representation of the patient's teeth;
ii. obtaining diagnostic data for one or more of the teeth;
iii. identifying individual teeth in the digital 3D representation;
iv. segmenting the individual teeth from the digital 3D representation;
v. deriving tooth condition information from the diagnostic data; and
vi. correlating the derived tooth information with the individual teeth.

Disclosed is a User Interface Configured for Populating a Digital Dental Chart with Tooth Condition Information for a Patient's Teeth, wherein the User Interface is Configured for:
obtaining a digital 3D representation of the patient's teeth;
identifying individual teeth in the digital 3D representation;
segmenting the individual teeth from the digital 3D representation;
obtaining diagnostic data for one or more of the teeth;
deriving tooth condition information from the diagnostic data;
correlating the derived tooth information with the individual teeth;
obtaining a digital dental chart comprising regions representing tooth surfaces;
correlating the individual teeth with the corresponding regions of the digital dental chart; and
adding a representation of the derived tooth condition information to the corresponding regions of the digital dental chart.

The digital 3D representation comprises shape data expressing the topography of 10 one or more of the patient's teeth. The segmentation and identification of the teeth is preferably based at least partly on these shape data. In some cases the digital 3D representation also comprises shape data for the patient's gingiva. Gingiva condition information can then be derived either independently or as part of the tooth condition information.

The digital 3D representation can be obtained by intraoral scanning, by scanning an impression of the patient's teeth or a physical model of the teeth formed using such an impression.

Some scanning technologies are capable of measuring both the shape of the tooth surface as well as internal structures inside the tooth. This is e.g. the case for X-ray based scanners, such as Cone Beam Computed Tomography scanners, and optical coherence tomography scanners. Such scanners can provide a digital 3D representation which contains both shape data for the topography of the tooth as well as data relating to the internal structure and sub-surface damages in the tooth and the presence of caries and dental restorations.

In some embodiments, at least part of the diagnostic data are comprised in the digital 3D representation. One advantage of this embodiment is that the diagnostic data and the tooth portions segmented from the digital 3D representation already are correlated. When the diagnostic data are comprised in the digital 3D representation they are often aligned with the shape data expressing the topography of the segmented teeth. For example tooth shade data can be recorded simultaneously with the shape data such that in the obtained digital 3D representation the shade data and shape data for the teeth are precisely correlated.

There is hence no need for an additional step of aligning the diagnostic data with the shape data of the digital 3D representation to provide or determine the spatial correlation between the two. In this case obtaining the digital 3D representation and obtaining the diagnostic data is performed as one step, i.e. the digital 3D representation and the diagnostic data are obtained in the same step of the method.

The diagnostic data can also be the shape data of the digital 3D representation, such as when the tooth condition relates to e.g. tooth wear or gingiva retraction where the condition can be determined from analysis of the shape data.

In some embodiments the digital 3D representation comprises shape data, color or shade data, and fluorescence data. Such digital 3D representation may comprise data in the form of (x, y, z, color data, fluorescence intensity data). Here (x,y,z) represents the coordinates in space for a point on the tooth surface, the color data and fluorescence intensity data provide information regarding the tooth color and fluorescence, respectively, measured from the (x,y,z) point of the tooth surface. The color data can e.g. be provided in (RGB) coordinates. The digital 3D representation then comprises data in the form of (x, y, z, R, G, B, fluorescence intensity).

In some embodiments, the diagnostic data and the digital 3D representation of the patient's teeth are recorded using different devices such that the diagnostic data initially are not part of the digital 3D representation. This may e.g. be the case when the digital 3D representation is recorded using an intra-oral scanner providing a surface scan of the teeth while the diagnostic data are X-ray data, such as data recorded using a CBCT scanner.

In some embodiments, at least part of the diagnostic data are comprised in a diagnostic data set obtained in addition to the digital 3D representation of the patient's teeth. At least part of the tooth condition information can then be derived from this diagnostic data set. Such a diagnostic data set may be used e.g. when diagnostic data are extracted from scanners which does not record sufficiently precise or detailed shape data for the tooth surface, or when the diagnostic data are provided in the form of 2D images. Other examples of diagnostic data that may be obtaining from a diagnostic data set are CBCT data, separately obtained fluorescence data and IR data.

In such cases it can be advantageous to determine the spatial correlation between the digital 3D representations and the diagnostic data, i.e. the spatial correlation between the digital 3D representation and the diagnostic data of the diagnostic data set. The correlation can e.g. be expressed as a transformation bringing the digital 3D representation and the diagnostic data into a common coordinate system with the correct relative arrangement. Determining this correlation may provide that the spatial relationship between tooth and/or gingiva condition information derived from the diagnostic data and the shape data of the digital 3D representation also is determined. This is advantageous e.g. when using a computer program product for mapping the derived tooth and/or gingiva condition information onto the digital dental chart.

The spatial correlation may e.g. be determined based on aligning portions of the digital 3D representation and the diagnostic data relating to the same surface either based on fiducial markers, landmark identification or aligning the surfaces using e.g. an Iterative Closest Point algorithm.

In some embodiments the digital 3D representation is formed from a first digital 3D representation comprising shape data for the teeth and a second digital 3D representation comprising the diagnostic data. When the spatial correlation between the first and second digital 3D representations has been determined a digital 3D representation can be formed that contains both the shape data of the first digital 3D representation and the diagnostic data of the second digital 3D representation.

The correlation between the derived tooth condition information and the identified individual teeth of the digital 3D representation can be based on the determined spatial relationship between the digital 3D representation and the diagnostic data set.

The segmentation of the teeth from the digital 3D representation preferably isolate the portions of the digital 3D representation corresponding to the individual teeth from the remaining part of the digital 3D representation. I.e. the data of the digital 3D representation relating to the individual teeth are isolated from each other and from other parts of the digital 3D representation such as parts relating to the patient's gingiva.

The segmentation step can be performed before or after the teeth have been identified. If performed before, the identification can be based on the segmented teeth. If performed after, the identification the segmentation can be based on the knowledge of which tooth the given part of the digital 3D representation relates to.

The segmentation can be realized both with and without user interaction. If the digital 3D representation is visualized in a display such as a computer screen an operator can use a pointing too, such as a computer mouse to mark the boundaries of the individual teeth on the digital 3D representation. The segmentation of the teeth from the digital 3D representation can then be based on the marked boundaries. Computer based algorithms can also be applied to identify e.g. the transition from tooth surface to gingiva and the boundary of a tooth at its contact with neighbor teeth such that the segmentation can be made without or with limited user interaction.

When the diagnostic data comprises texture data, such as color data, the segmentation can also be based at least partly on the diagnostic data. For example the boundary of the tooth at the gingiva can be detected from the difference in the color of teeth and gingiva. In some embodiments, the tooth condition information for a tooth is derived from variations in the diagnostic data over the segmented tooth portion of the digital 3D representation. When the diagnostic data are comprised in the digital 3D representation, the diagnostic data are inherently linked to the shape data for the teeth. In some cases, such as when the tooth condition is the presence of caries in a given part of a tooth derived from a local variation in the fluorescence emitted from that tooth, the derived tooth condition information is already correlated with the tooth portion of the digital 3D representation. In some embodiments, the diagnostic data represents an intensity of a signal recorded from the teeth and variations in the intensity over the tooth surfaces indicates the presence of e.g. caries or an existing dental filling. The presence of a tooth condition can both be indicated by an increase or a decrease in the intensity of the signal at the location of the condition.

When sound teeth are illuminated by light with wavelength around 405 nm the teeth emits fluorescence with a broad emission at 500 nm that is typical of natural enamel. In caries infected areas of teeth additional peaks are often seen at 635 nm and 680 nm due to emission from porphyrin compounds in oral bacteria. I.e. the presence of caries can be detected by measuring whether the fluorescence signal at 635 nm and 680 nm recorded from a particular area of a tooth is stronger than from other (healthy) parts of the tooth. The increased strength of the fluorescent signal then provide a direct representation of caries in a tooth.

A decrease in the natural fluorescence emitted at 500 nm from teeth illuminated by light at wavelength of e.g. 405 nm can be caused by scattering in a region with caries. Detecting a lower fluorescence signal (around 500 nm) can thus be an indication of the presence of caries in that area of the tooth.

The diagnostic data may express a spatial distribution of the tooth condition. This may be the case when the diagnostic data are fluorescence data showing that a tooth is attacked by caries at a specific region of the tooth, e.g. the in a particular region on the occlusal surface.

In some embodiments, the tooth condition information comprises the location of the condition on the tooth. The derived information thus describes both the condition and which part of the tooth is affected by the condition. In the case of caries the tooth condition information may then comprise information describing that caries is present in the tooth and that it e.g. is located on the occlusal surface of the tooth.

When the digital 3D representation and/or the diagnostic data comprises data for the patient's gingiva the method may comprise deriving information relating to the condition of the gingiva, such as its shape, color, spatial relationship to the teeth, or the depth of the gingival pockets. Monitoring the gingiva shape and its spatial relationship to the teeth over time provides a means for detecting gingiva retraction and deepening of the gingival pockets.

In some embodiments, identifying the individual teeth comprises comparing the segmented teeth with digital template teeth of a tooth database. This is possible since different teeth have different shapes (e.g. an anterior tooth does not have the same shape as a posterior tooth). Whether a given molar tooth belongs to the left or right side of the patient's mouth can e.g. be determined from the location of the corresponding data in the digital 3D representation of the patient's teeth.

When the teeth have been identified the result of the identification can be visualized in a user interface allowing an operator to confirm that the identification is correct.

In some embodiments, the teeth are manually identified by an operator using e.g. a pointing tool on a visualization of the set of teeth in a user interface. The dentist or operator often sees a visualization of the teeth during a procedure and manually identifying the individual teeth can be made using a pointing tool in connection with a visualization of the teeth on a display.

In some embodiments, the identification of the teeth in the obtained digital 3D representation is based on an identification made for a previously obtained digital 3D representation of the patient's teeth. This previously obtained digital 3D representation may have been analyzed while applying the method during a previous visit at the dentist. The previous analysis provides knowledge of the actual shape of this particular patient's teeth such that the teeth portions of the digital 3D representation obtained during the current visit can be compared with the actual shape. Such comparison is potentially easier and more precise than a comparison with template teeth of a tooth data base. In some embodiments, the shapes of the identified teeth are stored in the electronic data record. This provides the advantage that the identification of the teeth during a subsequent use of the method, such as during a subsequent visit at the dentist, can be based on the actual shape of the patient's set of teeth. Such identification is potentially much faster and requires less computational force compared to when e.g. the teeth are identified based on a comparison with standard teeth shapes.

In some embodiments, the diagnostic data comprises data selected from the group consisting of texture data, such as tooth color data or tooth shade data, fluorescence data, Infrared data, X-ray data, optical coherence tomography data, ultrasound data, laser speckle images, or data representing the occlusal contacts between antagonist teeth. In principle any kind of data suitable for diagnostic purposes and for expressing the condition of the teeth can be used.

In the context of the present disclosure the phrase "Fluorescence data" refers to data acquired by a fluorescence measurement detecting a fluorescent signal emitted from the tooth in response to illumination by a probe beam comprising light at wavelengths capable of exiting fluorescent material of or at the teeth. The excitation may e.g. use blue or green light depending on which material is to be excited.

In the context of the present disclosure the phrase "Infrared data" refers to data acquired by an infrared measurement, e.g. by an infrared scanner, where the transmission or variations in the transmission of light at Infrared wavelengths through the analyzed tooth or teeth are detected. Variations in the intensity of the infrared light transmitted through a tooth can e.g. be due to dental fillings, cracks in the tooth surface or caries.

Occlusal contacts with antagonist teeth can e.g. be determined using a virtual articulator mimicking the relative movement of the teeth during the bite. The occlusal contacts can also be recorded using articulating paper which leaves color markings on the teeth. If the digital 3D representation of the teeth is acquired using an intra-oral scanning recording both teeth shape and color the contact points can be derived from the digital 3D representation. The derived occlusal contact can then be mapped onto the digital dental chart.

The X-ray data can e.g. be in the form of cone-beam computed tomography image or 2D X-ray images.

In some embodiments the derived tooth condition information relates to information selected from the group consisting of tooth shade, tooth wear, caries, presence of cariogenic bacteria, presence of fillings from previous dental work, acid erosion damages, bruxism induced damages, tooth arrangement, malocclusion or gingiva retraction.

The tooth arrangement can be derived as part of an orthodontic treatment wherein the changes in the arrangement of the patient's teeth is monitored. Storing the tooth condition information, i.e. the tooth arrangement, derived for the patient's teeth during the treatment then provides a strong tool for the orthodontist in visualizing the progress and for confirming that the treatment progresses as planned.

Damages caused by acid erosion or bruxism can be detected from laser speckle images providing information on the microstructure of the enamel. Such damages can also be detected to monitor the change in the shape of the patient's teeth over time.

The presence of cariogenic bacteria or fractures on a microstructure scale can be indicators of developing caries in the tooth.

Information can be derived for several teeth and with respect to several different dental conditions.

In some embodiments, the operator will manually annotate the derived tooth condition information onto the digital dental chart.

In some embodiments, the method comprises obtaining a digital dental chart comprising regions representing surfaces of the patient's teeth and adding a representation of the derived tooth condition information to the region or regions of the digital dental chart corresponding to the tooth or teeth for which the dental condition information is derived. In some embodiments the digital dental chart comprises regions representing tooth surfaces, i.e. for each of the teeth normally found in a patient's set of teeth the digital dental chart has one or more regions representing the surfaces of the tooth. For the anterior teeth the digital dental chart may comprise a region representing the labial surface and a region representing the lingual surface of each tooth. For each of the posterior teeth the digital dental chart may comprise a region representing the buccal surface, a region representing the lingual surface and a region representing the occlusal surface. E.g. if caries is detected in one of the canines a representation showing the dentist that carries is present in that tooth is added to the regions of the dental chart representing this tooth.

In some embodiments, the digital dental chart comprises a 2D dental chart with regions representing the different surfaces of the teeth. The diagnostic data or the derived tooth condition information for a segmented tooth may then be projected onto the corresponding region in the digital dental chart. The region can e.g. represent a buccal/labial, an occlusal or a lingual surface of the teeth in the digital dental chart.

The digital dental chart may be in the form of a standard dental chart wherein the regions representing the different teeth are generalized.

In some embodiments, the regions are formed based on the corresponding surfaces of the teeth such that the digital dental chart is a personalized dental chart wherein the regions of the dental chart are shaped and/or colored and/or arranged according to the actual situation in the patient's mouth.

In some embodiments, adding the derived tooth condition information to the digital dental chart comprises mapping a representation of the derived information onto the digital dental chart. The tooth condition information is then visualized at the correct region in the digital dental chart.

In some embodiments, the diagnostic data are mapped onto the digital dental chart. For example shade data or fluorescence data can be mapped onto the regions of the digital dental chart such that the digital dental chart shows the tooth surface representations with the diagnostic data projected onto the regions.

In some embodiments, the diagnostic data comprises texture data and a representation of the texture data is projected onto the regions of the digital dental chart representing the surfaces of the teeth.

Derived information regarding the condition of the patient's gingiva may also be added to the digital dental chart. The gingiva condition information may be mapped onto the digital dental chart.

Tooth condition information derived manually, such as from of separate images X-ray images, may be manually annotated on the digital dental chart.

In some embodiments, the tooth condition information is represented on the digital dental chart using a color code, geometrical or text symbols, a vector map, or one or more arrows. Such arrows can e.g. be used to indicate a movement since last update of the chart when the digital dental chart is used to monitor an orthodontic treatment. Populating the digital dental chart may thus comprise projecting a symbol for the information onto the corresponding region of the digital dental chart.

In some embodiments, the digital dental chart is formed at least partly from the digital 3D representation.

This provides an advantage when the diagnostic data are comprised in the digital 3D representation of the teeth since the correlation between the digital dental chart and the digital 3D representation established or used when forming the digital dental chart also can be used for the mapping of the derived tooth condition information or the diagnostic data onto the digital dental chart.

In some embodiments, the digital dental chart is obtained by loading a dental chart template into a computer system configured for executing the instructions of a computer program product that provides the steps of the disclosed methods.

Disclosed is a Method for Deriving Tooth Condition Information for a Patient's Teeth, wherein the Method Comprises:
 loading a digital 3D representation of the patient's teeth and diagnostic data for one or more of the teeth into an electronic data processing device, and
 executing a computer program product using said electronic data processing device, where the computer program product comprises computer readable instructions for:
  identifying the individual teeth in the digital 3D representation;
  segmenting the individual teeth from the digital 3D representation;
  deriving tooth condition information from the diagnostic data; and
  correlating the derived tooth information with the identified individual teeth.

Disclosed is a Method for Deriving Tooth Condition Information for a Patient's Teeth, wherein the Method Comprises:
 loading a digital 3D representation of the patient's teeth and diagnostic data for
 one or more of the teeth into a digital environment; and
 in the digital environment performing the steps of:
  identifying the individual teeth in the digital 3D representation;
  segmenting the individual teeth from the digital 3D representation;
  deriving tooth condition information from the diagnostic data; and
  correlating the derived tooth information with the identified individual teeth.

Disclosed is a Computer Program Product Comprising Computer Readable Instructions for:
 obtaining a digital 3D representation of the patient's teeth;
 obtaining diagnostic data for one or more of the teeth; and
 deriving tooth condition information for the patient's teeth by a procedure comprising:
  identifying the individual teeth in the digital 3D representation;
  segmenting the individual teeth from the digital 3D representation;
  deriving tooth condition information from the diagnostic data; and
  correlating the derived tooth information with the identified individual teeth.

Disclosed is a Computer Program Product Comprising Computer Readable Instructions which when Executed by an Electronic Data Processing Device Provides a Digital environment for deriving tooth condition information for a patient's teeth by a method comprising:
 loading a digital 3D representation of the patient's teeth into the digital environment;
 identifying the individual teeth in the digital 3D representation;
 segmenting the individual teeth from the digital 3D representation;
 loading diagnostic data for one or more of the teeth into the digital environment;
 deriving tooth condition information from the diagnostic data; and
 correlating the derived tooth information with the identified individual teeth.

In some embodiments, the computer readable instructions perform one or more of the steps of the method when executed, such as the steps of identifying, segmenting, deriving, and correlating.

Disclosed is a computer program product comprising computer readable instructions for providing a virtual environment comprising a user interface, where the virtual environment is configured for:
 obtaining a digital 3D representation of the patient's teeth and displaying the digital 3D representation in the user interface;
 obtaining diagnostic data for one or more of the teeth; and
 assisting a user in deriving tooth condition information for the patient's teeth by a procedure comprising:
  i. identifying the individual teeth in the digital 3D representation;
  ii. segmenting the individual teeth from the digital 3D representation;
  iii. deriving tooth condition information from the diagnostic data; and
  iv. correlating the derived tooth information with the individual identified teeth.

In some embodiments, the virtual environment is configured for displaying the diagnostic data or a digital diagnostic data file containing the diagnostic data in the user interface. Disclosed is a non-transitory computer readable medium encoded with the disclosed computer program product.

In some embodiments, the electronic data record is configured for being loaded into a dental practice management system.

The dental practice management system can then preferably read the tooth condition information from the electronic data record such that the dental practice management system e.g. can visualize the derived tooth condition information in a digital dental chart.

The dental practice management system may also be configured for comparing the tooth condition information and/or gingiva condition information of the loaded electronic data record with information derived from diagnostic data obtained at an earlier time. The digital dental chart can e.g. be visualized in a user interface of the dental practice management system.

In some embodiments the user interface is configured for toggling between displaying the digital dental chart and displaying the digital 3D representation of the teeth. The digital dental chart can e.g. comprise a 2D dental chart with regions visualizing the visible surfaces of the patient's teeth where the derived information is mapped onto these regions, while the digital 3D representation shows both shape and e.g. shade or fluorescence data obtained from the teeth.

This provides the advantage that the operator, such as a dentist, easily can change between the different views and thereby have easy access to the different knowledge provided by the different views.

The toggling between the different views can e.g. be provided when a virtual push button is pressed or activated in any other suitable way.

In some embodiments, the user interface is configured for toggling between displaying the digital dental chart with the derived tooth information visualized in the corresponding regions and displaying the digital dental chart with the derived information hidden. This can be advantageous when the texture data, such as color or tooth shade, is visualized on the digital dental chart. Toggling then allows one view to be with the digital 3D representation with e.g. shade data clearly visible without interfering with tooth condition information and another view providing the tooth condition information.

In some embodiments, one view of the dental chart comprises the digital 3D representation with only shape data and with tooth condition information mapped onto the regions of the digital 3D representation.

This provides the advantage that the tooth condition information is seen on a digital 3D visualization of the teeth but without any texture data interfering with the tooth condition information.

In some embodiments the digital 3D representation is recorded while a bite wing is arranged at the patient's teeth and the method comprises registering a digital model of the bite wing with the digital 3D representation to derive the information of the bite wing relative to the patient's teeth.

The disclosed embodiment can be used both for adding tooth and gingiva condition information to a clean digital dental chart or for updating an existing digital dental chart for the patient. I.e. the obtained digital dental chart may be a clean template digital dental chart or a previously populated digital dental chart already comprising diagnostic data or tooth condition information for the patient's teeth such that generating the digital dental chart provides an updated digital dental chart for the patient's teeth.

Disclosed is a Method for Deriving Tooth Condition Information for a Patient's Teeth, wherein the Method Comprises:
  obtaining a digital representation of the patient's teeth;
  identifying the individual teeth in the digital representation;
  segmenting the individual teeth from the digital representation;
    obtaining diagnostic data for one or more of the teeth;
    deriving tooth condition information from the diagnostic data; and
    correlating the derived tooth information with the individual teeth.

In some embodiments, the digital representation of the teeth comprises a digital 2D representation or a digital 3D representation of the teeth.

Furthermore, the disclosure relates to a computer program product comprising computer readable instructions for causing a data processing system to perform the method according to any of the embodiments when said computer readable instructions are executed on the data processing system, and a computer program product, comprising a computer-readable medium having stored there on the computer readable instructions. Disclosed is a non-transitory computer readable medium storing thereon a computer program, where said computer program is configured for causing computer-assisted deriving of tooth condition information for a patient's teeth, wherein the deriving comprises identifying the patient's individual teeth in and segmenting the individual teeth from an obtained digital 3D representation of the patient's teeth, and deriving tooth condition information for the individual teeth from diagnostic data obtained for one or more of the teeth.

The present invention relates to different aspects including the method, computer program products, systems, digital environments, and user interfaces described 20 above and in the following, and corresponding methods, computer program products, systems, and/or user interfaces, each yielding one or more of the benefits and advantages described in connection with the first mentioned aspect, and each having one or more embodiments corresponding to the embodiments described in connection with the first mentioned aspect and/or disclosed in the appended claims.

EMBODIMENTS

1. A method for populating a digital dental chart with tooth condition information, wherein the method comprises:
  deriving tooth condition information for one or more of the teeth by using
  the method according to any one of the disclosed embodiments;
  obtaining a digital dental chart comprising regions representing tooth surfaces;
  correlating the identified and segmented teeth with the corresponding regions of the digital dental chart; and
  adding a representation of the derived tooth condition information to the corresponding region or regions of the digital dental chart.

2. The method according to embodiment 1, wherein adding the derived tooth condition information to the digital dental chart comprises mapping the representation of the derived information onto the digital dental chart.

3. The method according to embodiment 1 or 2, wherein the tooth condition information is represented on the digital dental chart using a color code, geometrical or text symbols, a vector map, or one or more arrows.

4. The method according to any of embodiments 1 to 3, wherein the digital dental chart is formed at least partly from the digital 3D representation.

5. The method according to any of embodiments 1 to 4, wherein the diagnostic data comprises texture data and a representation of the texture data is projected onto the regions of the digital dental chart representing the surfaces of the teeth.

6. The method according to embodiment 5, wherein the digital dental chart comprises a 2D dental chart with regions representing the different surfaces of the teeth and where the diagnostic data or the derived tooth condition information for a segmented tooth are projected onto the corresponding region in the digital dental chart.

A method for generating an electronic data record configured for use in a dental practice management system, where the electronic data record comprises tooth condition information for the individual teeth of a patient, wherein the method comprises:
  deriving tooth condition information for one or more of the teeth by using the method of any one of the disclosed embodiments; and
  storing the tooth condition information for the identified teeth in the electronic data record.

8. The method according to embodiment 7, wherein the shape data for the segmented and the identified teeth are stored in the electronic data record.

9. The method according to embodiment 7 or 8, wherein the electronic data record is configured for being loaded into a dental practice management system.

10. A virtual environment configured for deriving tooth condition information for a patient's teeth, wherein the virtual environment is configured for:
obtaining a digital 3D representation of the patient's teeth;
identifying the individual teeth in the digital 3D representation;
segmenting the individual teeth from the digital 3D representation;
obtaining diagnostic data for one or more of the teeth;
deriving tooth condition information from the diagnostic data; and
correlating the derived tooth information with the individual teeth.

11. The virtual environment according to embodiment 19, wherein the tooth condition information is visualized on the digital dental chart using a color code, geometrical or text symbols, a vector map, or one or more arrows.

12. The virtual environment according to embodiment 20, wherein the virtual environment is configured for toggling between displaying the digital dental chart and displaying the digital 3D representation.

13. The virtual environment according to embodiment 20 or 21, wherein the virtual environment is configured for toggling between displaying the digital dental chart with the derived tooth information visualized in the corresponding regions and displaying the digital dental chart with the derived information hidden.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein.

DETAILED DESCRIPTION

In the following description, reference is made to the accompanying figures, which show by way of illustration how the invention may be practiced.

Figure 1:
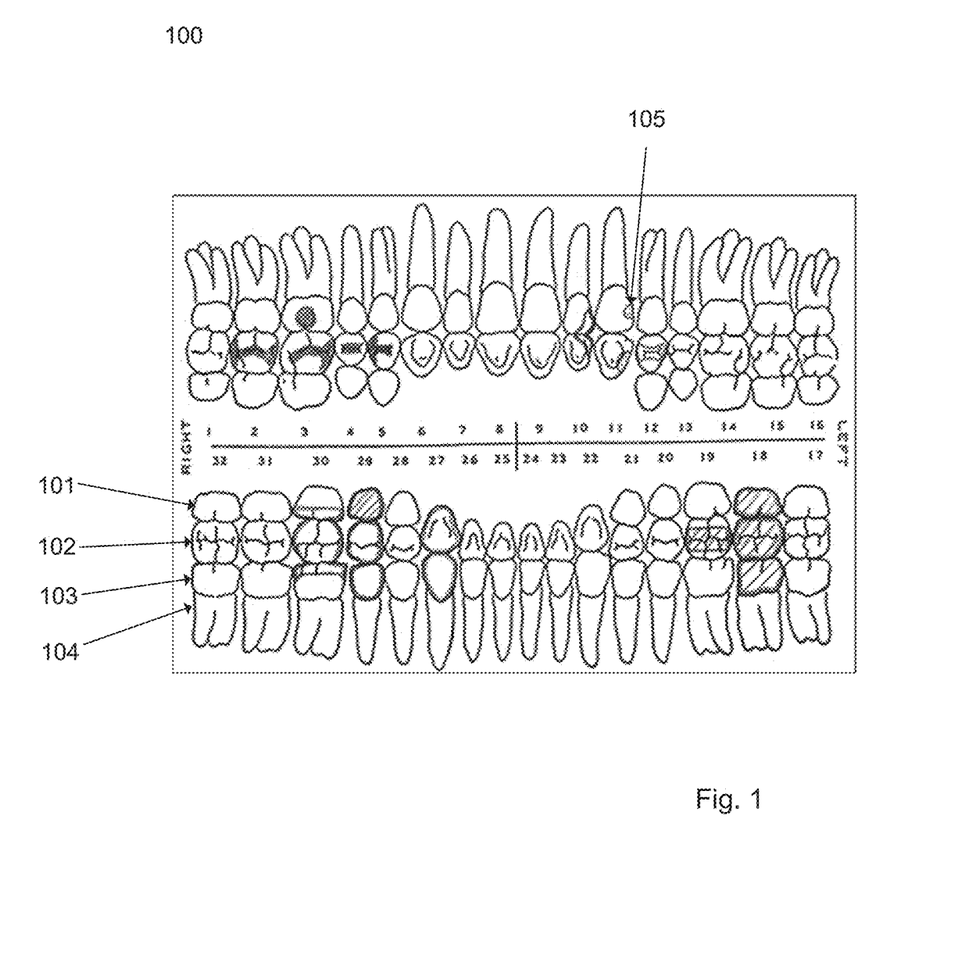
FIG. 1 shows a dental chart used for recording tooth condition information.

FIG. 1 shows a dental chart used for recording tooth condition information. This dental chart 100 has standardized regions representing the surfaces and the root of each tooth. For example the dental chart 100 has regions 101, 102 and 103 representing the lingual, occlusal and buccal surfaces, respectively, of tooth #32 while region 104 represents the roots of that tooth.

The regions representing the tooth surfaces can be shaped to resemble the teeth even more than seen in FIG. 1 or be more schematic. Most dental charts has regions for all teeth usually found in the human mouth as also seen in the chart illustrated in FIG. 1. Different symbols can be used for visualizing the tooth condition information derived for the patient's teeth. In the dental chart of FIG. 1 there is among other things a composite filling in tooth 11 symbolized by a ring filled with dots 105.

Figure 2:
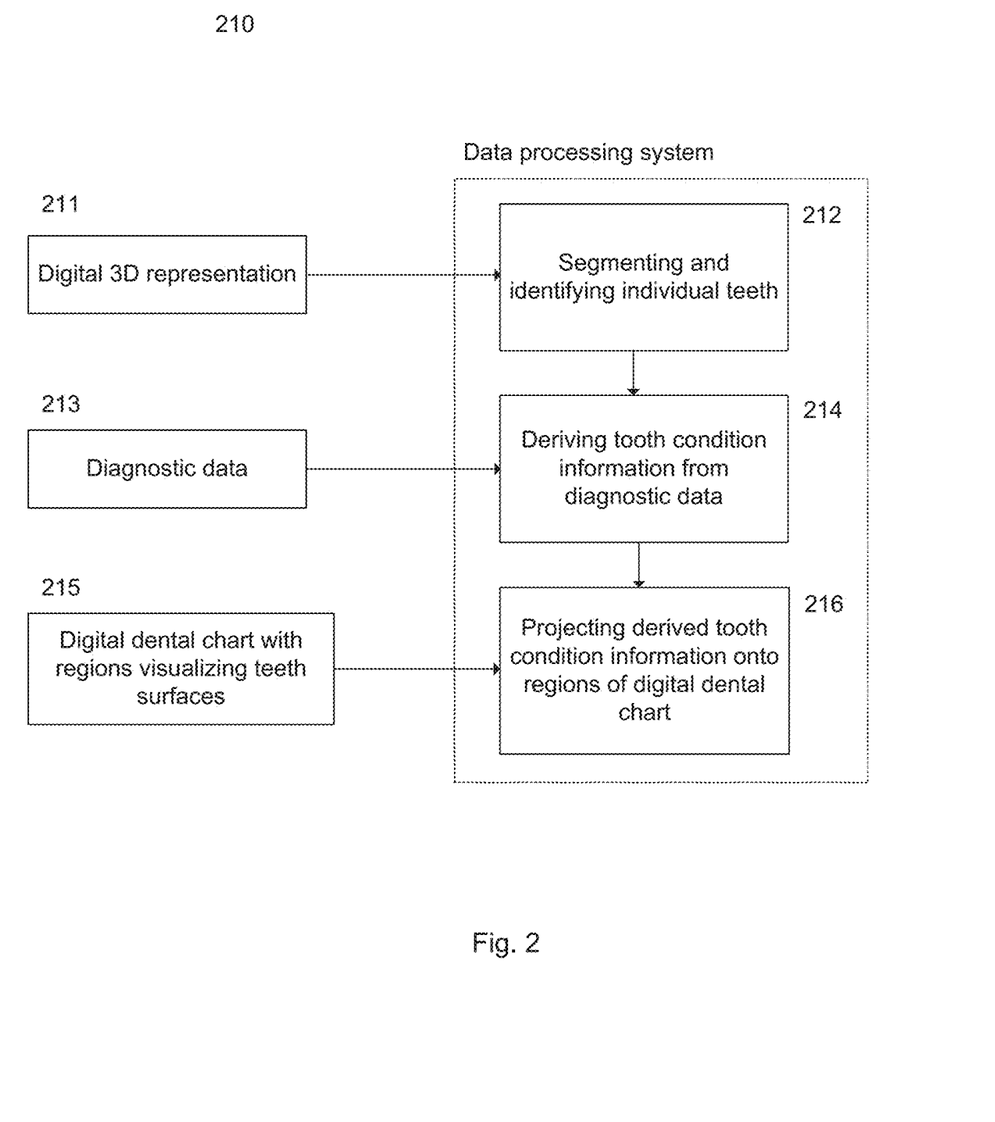
FIG. 2 shows a schematic of a flowchart.

Such dental charts have been known for decades in paper form and are also part of many digital dental practice management systems where a digital dental chart is used. FIG. 2 shows a schematic of a flowchart 210 for an embodiment.

In step 211 the digital 3D representation of the patient's teeth with the shape data describing the topography of the teeth is obtained. The digital 3D representation can be recorded using an intra-oral scanner, such as the TRIOS intra-oral scanner produced by 3shape A/S or by scanning an impression of the teeth or a physical model if the teeth manufactured from the impression.

The digital 3D representation is loaded into a data processing system having a non-transitory computer readable medium encoded with a computer program product having computer readable instructions for identifying and segmenting the individual teeth from the remaining parts of the digital 3D representation (step 212). These operations provide that digital models of the individual teeth are obtained and given the corresponding teeth number.

The tooth identification can be handled by tooth recognition algorithms executed by the data processing system where e.g. the digital models of the individual teeth are compared with standardized teeth CAD models for the different types of teeth normally found in person's mouth. The identification can also be based on symmetry across the patient's medial plane which provides a reference for the teeth numbering.

In step 213 the diagnostic data for the teeth is obtained. The diagnostic data can e.g. be color data, shade data, fluorescence data, Infrared data, Cone beam computed tomography (CBCT) data, and occlusal contact data.

FIG. 2 illustrates obtaining of the digital 3D representation 211 and the diagnostic data 213 as separate steps. However this is not necessarily the case since some diagnostic data may be obtained as part of the digital 3D representation, i.e. such that actions of steps 211 and 213 are performed in one single step. If for example an intra-oral scanner is configured for recording color, such as the TRIOS 3 intra-oral scanner, diagnostic data in the form of color or shade data can be recorded simultaneously with the shape data of the digital 3D representation. The obtained digital 3D representation then comprises both shape data and diagnostic data for the teeth.

The diagnostic data are also loaded into the data processing system and in step 214 tooth condition information is derived from the obtained diagnostic data. The analysis for deriving the tooth condition information depends on the character of the diagnostic data and the information that is being derived.

In case the diagnostic data are fluorescence data the derived information can relate e.g. to the presence of caries or cariogenic bacteria in a part of the patient's tooth or the presence of fillings or dental restorations. Cariogenic bacteria produce porphyrin compounds which emit a fluorescent signal at wavelengths above 600 nm in response to excitation by a probe light at wavelength of 405 nm. If the porphyrin compounds are present on part of the tooth surface there will be a stronger fluorescent signal from that part of the tooth surface and the cariogenic bacteria are detected from the local increase in the intensity of the fluorescence.

The fluorescence data can be recorded as part of the digital 3D representation using a scanner which detects the shape data based on probe light reflected from the teeth surfaces and simultaneously records the longer wavelength fluorescent signal. This can be realized if the probe light is provided by a blue LED or laser emitting light at a wavelength of 405 nm and the detector of the scanner applies a Bayer filter to distinguish between the reflected light and the fluorescent signal. In that case the fluorescence data can be recorded simultaneously with the reflected light and the recorded digital 3D representation comprises both shape data and the fluorescence data.

The analysis of the diagnostic data can be made by an operator based on a visualization of the diagnostic data e.g. in a user interface for configured for assisting the operator in performing steps of the method. For instance diagnostic data in the form of Infrared data for the patient's teeth can be presented in the user interface and the operator can identify tooth sections scattering the infrared light as e.g. caries or fractures in the enamel of the tooth.

The analysis can also be performed by a computer program product having instructions for detecting variations in e.g. the intensity of the diagnostic data over the tooth. For example the scattering of infrared light by a fracture in the enamel will cause a locally lower intensity of the transmitted infrared light. The presence and position of such a local intensity minimum can be derived by the computer program product whereby the tooth condition information is derived from the analyzed diagnostic data.

In step 215 the digital dental chart is obtained. This can be obtained from a database of a dental practice management system and either be a clean template for the recording of tooth condition information at a patient's first visit at the clinic or t can be a digital dental chart already populated with such information at one or more previous visits at the clinic. The digital dental chart can have standardized representations of the patient's teeth as the one illustrated in FIG. 1.

In step 216 the obtained digital dental chart is populated with the derived tooth condition information. When the information has been derived from diagnostic data which are spatially correlated with the digital 3D representation, i.e. the spatial correlation of the diagnostic data and the shape data of the digital 3D representation is known, the derived information can immediately be projected onto the corresponding regions of the digital dental chart. If this spatial correlation is not established it is also possible for the operator to manually annotate the derived information on the digital dental chart e.g. using a computer mouse to indicate where on a tooth region of the dental chart the tooth condition information should be added. If gingiva condition information, such as presence of inflammation or pocket depth, has been derived from the diagnostic data this information can also be added to the digital dental chart.

Steps 211 to 214 alone relates a method for deriving tooth condition information while steps 211 to 216 relates to a method for deriving the tooth condition information and populating a digital dental chart with the derived information.

The steps can be performed by a system having a non-transitory computer readable medium capable of receiving and storing the digital 3D representation of the patient's teeth, the diagnostic data for one or more of the teeth, and the digital dental chart. A computer program product is also stored on the medium where the computer program product has instructions for deriving the tooth condition information and for populating the digital dental chart with the derived tooth condition information. The graphical representation of the populated digital dental chart can be displayed on a display unit of the system. Such a system described in relation to FIG. 4.

FIGS. 3A, 3B, 3C and 3D illustrate steps for deriving tooth condition information and populating a digital dental chart with the derived information.

Figure 3A:
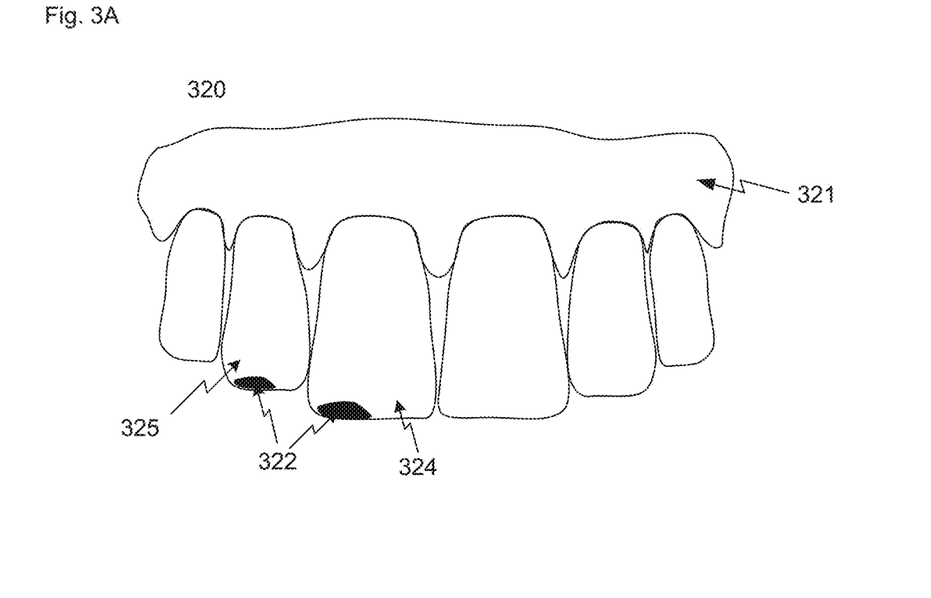
FIGS. 3A, 3B, 3C and 3D illustrate steps of an embodiment.

FIG. 3A shows a schematic of an obtained digital 3D representation 320. The digital 3D representation can be visualized in a digital work space presented to the operator on a display such as a computer screen. The digital 3D representation 320 has shape data for the surfaces of part of the gingiva 321 and the six anterior teeth of the patient's upper jaw, i.e. teeth #6 to #11 in the Universal tooth numbering system. In addition to the shape data expressing the topography of the teeth the digital 3D representation 320 also provides diagnostic data in the form of fluorescence data. The fluorescence data has significantly stronger intensities in two sections 322 on the patient's maxillary central incisor 324 and maxillary lateral incisor 325. The fluorescence data can e.g. be from fluorescence emitted at wavelengths above 600 nm from porphyrin compounds when these are excited by light at 405 nm. As described above porphyrin compounds indicate that cariogenic bacteria are present.

The digital 3D representation can be obtained by an intra-oral scanner using a blue LED to illuminate the patient's teeth. The topography of the teeth can be derived from the blue light reflected from the teeth surface while tooth condition information is derived from the red light emitted by fluorescent materials in the infected regions 322 in response to the blue light. This provides that the fluorescence data, i.e. the diagnostic data, are obtained simultaneously with the shape data and that the 25 fluorescence data are part of the digital 3D representation and according are spatially correlated with the shape data for the teeth.

Figure 3B:
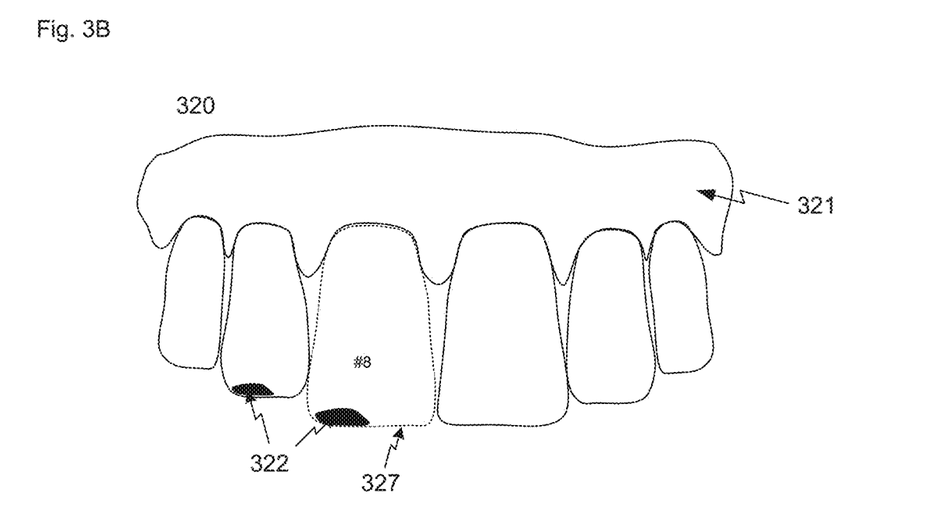
Figure 3C:
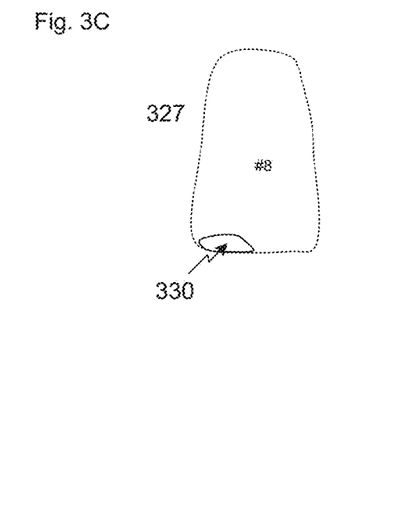

FIG. 3B shows the obtained digital 3D representation 320 with the maxillary central incisor segmented from the digital 3D representation. The segmented portion forms a digital model 327 of the maxillary central incisor (tooth #8) shown as a dotted line in the figure. The segmentation of the teeth from the digital 3D representation involves a detection of the boundaries of the surfaces for each tooth. The boundary at the gingiva can be detected based on the shape data of the digital 3D representation or on color data of the digital 3D representation. The segmentation can be performed by a computer program product having instructions configured for detecting the boundaries in the digital 3D representation or by an operator marking the boundaries on the digital 3D representation. The boundaries detected by the computer algorithm can also be visualized in a digital work space such that the operator can verify that the detected boundaries are correct. The individual teeth are identified using a computer program product configured for making the identification from the digital 3D representation. This can be realized based on an analysis of the shape of the segmented teeth and/or by a comparison with templates teeth describing standard shapes and relative sizes of the teeth. If the digital 3D representation has shape data for the central incisors these can be detected based on their symmetry and the remaining teeth identified based on their natural position relative to the central incisors. In FIG. 3B the segmented tooth is identified as tooth #8 using the Universal tooth numbering system. Instead of using a computer program product the operator can manually identify each tooth using e.g. a pointing tool in connection with the digital work space.

When the fluorescence data are obtained as part of the digital 3D representation the spatial correlation between the fluorescence data and the shape data is known. If the analysis of the fluorescence data concludes that the fluorescent signal recorded from some sections of the teeth, such as sections 322 at the incisal edges of the maxillary central incisor 324 and maxillary lateral incisor 325, is significantly stronger than the fluorescent signal from other parts of the teeth it is concluded that there is a risk that cariogenic bacteria are present in these sections. I.e. based on the fluorescence data the system or the operator derives the tooth condition information that caries probably is present or developing in sections 322 on the maxillary central incisor 324 and maxillary lateral incisor 325. The derived information is visualized using a symbol 330 on the digital model of the segmented tooth 327 as illustrated on FIG. 3C.

Figure 3D:
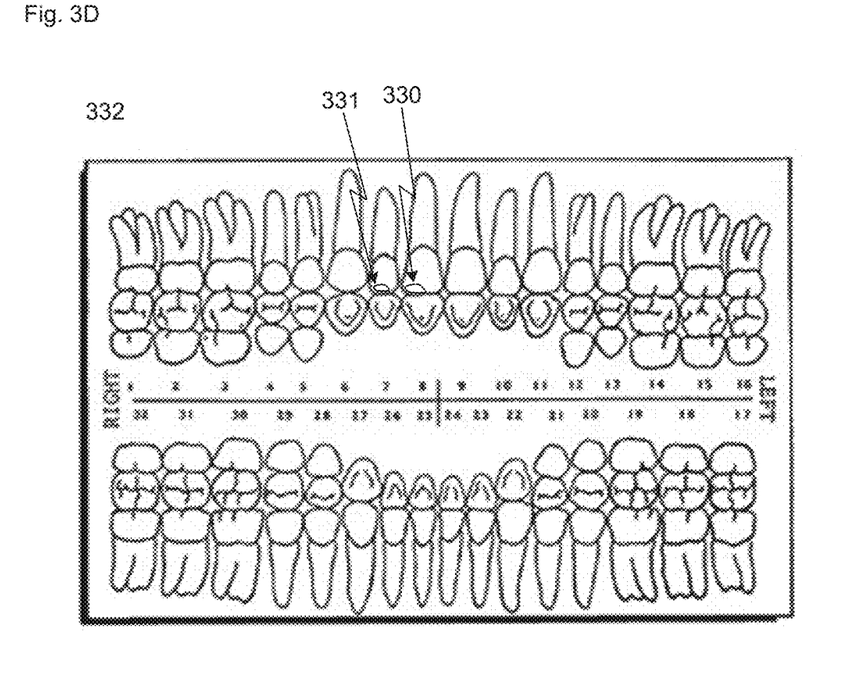

FIG. 3D shows symbols 330, 331 for the tooth condition derived for the maxillary central and lateral incisors projected onto the corresponding regions of a digital dental chart 332 like the one described in FIG. 1. The thereby populated digital dental chart can be stored and examined e.g. at the next visit at the dental clinic to determine what has changed since the last visit.

Figure 4:
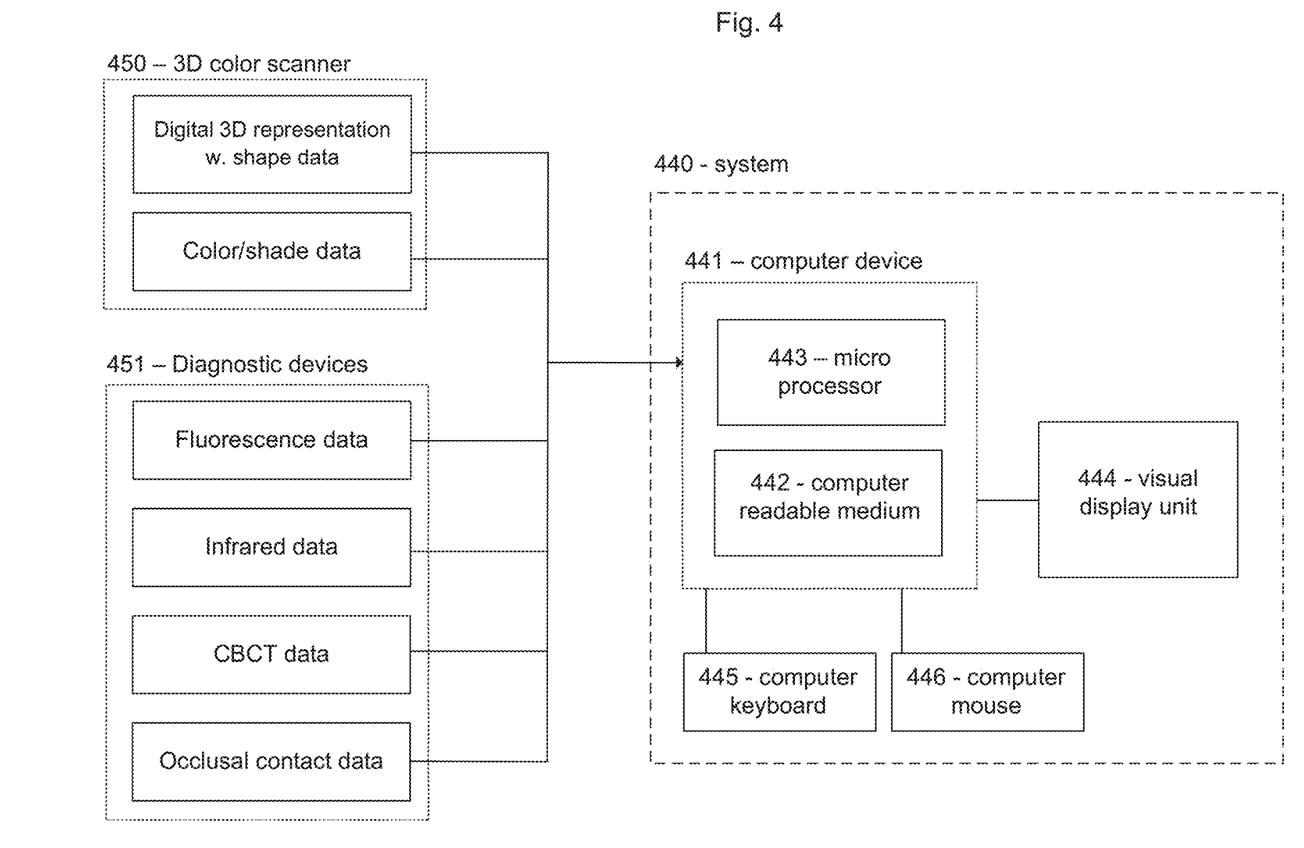
FIG. 4 shows a system according to an embodiment.

FIG. 4 shows a schematic of a system according to an embodiment. The system 440 comprises a computer device 441 comprising a computer readable medium 442 and an electronic data processing device in the form of a microprocessor 443. The system further comprises a visual display unit 444, and at least one access device and/or interface that allow the operator to utilize the functionality of the computer system. The access device and/or interface can include but is not limited to a keyboard, mouse, touch screen, stylus, joystick, light pen, trackball, voice interactive function, three-dimensional glove, solid three-dimensional mouse ball, graphical user interface (GUI), display screen, printer, and other known input or output devices and interfaces. In FIG. 4 the access devices are a computer keyboard 445 and a computer mouse 446 for entering data and activating virtual buttons of a user interface visualized on the visual display unit 444. The visual display unit 444 can e.g. be a computer screen. The computer device 441 is capable of obtaining a digital 3D representation of the patient's teeth and diagnostic data which both can be stored in the computer readable medium 442 and loaded to the microprocessor 443 for processing. The digital 3D representation can be obtained from a 3D color scanner 450, such as the TRIOS 3 intra-oral scanner manufactured by 3Shape TRIOS A/S, which is capable of recording both shape and color of the teeth.

The computer system provides for the execution of the method steps by which the acquired digital 3D representation can be manipulated, either automatically or in response to operator commands. The computer may be a general purpose computer capable of running a wide variety of different software applications or a specialized device limited to particular functions. In some embodiments, the computer is a network or other configuration of computing devices. The computer may include any type, number, form, or configuration of processors, system memory, computer-readable mediums, peripheral devices, and operating systems.

In one embodiment, the computer includes a personal computer (PC), which may be in the form of a desktop, laptop, tablet PC, or other known forms of personal computers. Diagnostic data can be recording using different types of diagnostic devices 451, such as an Infrared scanner and a CBCT scanner for recording infrared and data CBCT data, respectively. The recorded data are loaded into the computer readable medium 442 and analyzed using the microprocessor 443 to derive the tooth condition information for the patient's teeth.

A digital dental chart containing previously recorded data for the patient is stored on the computer readable medium 442 from where it can be loaded into the microprocessor 443 and visualized on the visual display 444 unit such that the dentist can recall the dental history of the patient.

The system 441 is configured for allowing an operator to arrange the digital 3D representation and the diagnostic data according to the spatial arrangement which best reflects to anatomical correct arrangement. This is relevant when the spatial correlation between the digital 3D representation and the diagnostic data is needed but not known. This can e.g. be the case when the diagnostic data are CBCT data which has been recorded independently of the digital 3D representation. The digital 3D representation and the diagnostic data can be moved relative to each other in three dimensions using e.g. a computer mouse to drag or rotate visualizations of the digital 3D representation and the diagnostic data on the visual display unit 444. When the operator is satisfied with the relative arrangement he activates a virtual push button in the user interface and the spatial relationship is stored in the computer readable medium 442.

Stored on the computer readable medium 442 is also computer program product having instructions for analyzing the diagnostic data to derive tooth condition information for the patient's teeth.

The computer readable medium 442 further stores a computer program product for the segmenting of teeth from the digital 3D representation and the identification of the individual teeth. When applied to the digital 3D representation the result is digital models of the individual teeth where the corresponding teeth numbers are known. These digital models of the individual teeth can be stored together with the digital dental chart in the patient's electronic journal on the computer readable medium 442 and be re-used at the next visit for the identification of individual teeth in a digital 3D representation recorded at the next visit.

When the spatial correlation between the digital 3D representation and the diagnostic data is know it is also known which tooth or teeth a given tooth condition information is derived for. Once the tooth condition information is derived it can thus be projected onto the digital dental chart visualized in the visual display unit 444. Thereby the dentist will have a useful tool for evaluating the patient's dental situation and to determine which treatments can be applied to correct for any problems.

Figure 5:
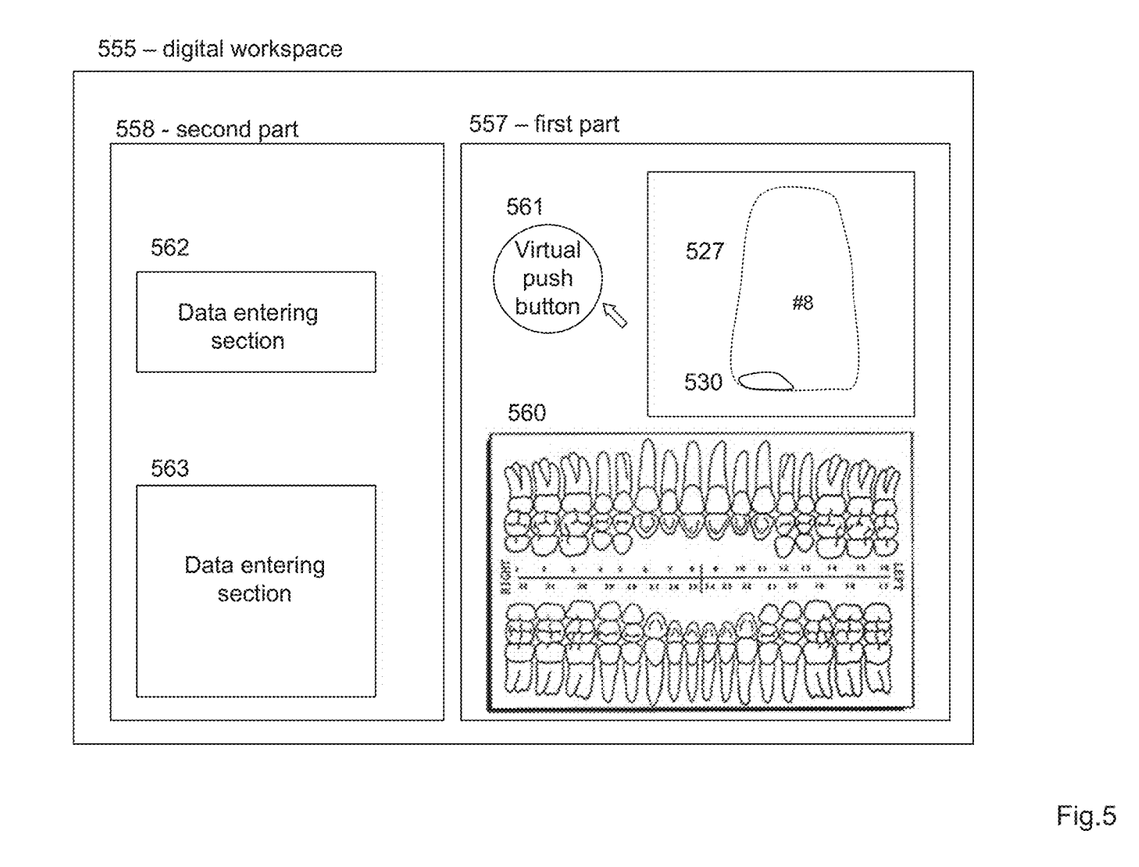
FIG. 5 shows user interface system according to an embodiment.

FIG. 5 shows a schematic of a digital work space of a digital environment according to an embodiment.

In a first part 557 of the digital workspace 555 a segmented tooth 527 from a digital 3D representation is illustrated. Tooth condition information 530 has been derived from obtained diagnostic data and is visualized on the segmented tooth. A digital dental chart 560 is also seen in the first part 557 of the digital workspace 555. When the operator has confirmed the derived tooth condition information a symbol for the information can be projected onto the digital dental chart 560 by activating the virtual push button 561. The virtual push button can e.g. be activated using a computer mouse button. The same mouse button can also be used for adjusting the position of the symbol on the region of the digital dental chart representing the tooth if the operator desires to do so.

The second part 558 of the digital workspace comprises data entering sections 562, 563 e.g. for entering the dentist's comments relating to the patient's dental situation, for selecting which diagnostic data to analyze and for choosing the digital dental chart which the tooth condition information is to be recorded on.

The digital workspace can be visualized on a visual display unit, such as a computer screen being part of a system configured for implementing the disclosed method.

The digital environment and workspace illustrated in FIG. 5 comprises one or more digital tools which can be displayed in the digital workspace. These digital tools allowing the operator to interact with the digital environment e.g. by entering data and to be part in at least one of the steps of identifying, segmenting, deriving and correlating. In FIG. 5 one of these tools is embodied as the virtual push button 561.

When activated the virtual push button causes the execution of instructions for populating the digital dental chart with the derived tooth condition information. Digital tools for segmenting and identifying the individual teeth from the digital 3D representation can be embodied by instructions of a computer program product allowing for an automatic segmentation and identification of the teeth.

Although some embodiments have been described and shown in detail, the invention is not restricted to them, but may also be embodied in other ways within the scope of the subject matter defined in the following claims. In particular, it is to be understood that other embodiments may be utilized and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

A claim may refer to any of the preceding claims, and "any" is understood to mean "any one or more" of the preceding claims.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

What is claimed is:

1. A computer implemented method for populating a digital dental chart with tooth condition information for a patient's teeth, wherein the method comprises:
   obtaining a digital three dimensional (3D) representation of the patient's teeth;
   obtaining diagnostic data for one or more of the teeth, wherein at least a part of the diagnostic data is comprised in a diagnostic data set obtained in addition to the digital 3D representation of the patient's teeth;
   deriving tooth condition information from the diagnostic data;
   determining a spatial correlation between the part of the diagnostic data of the diagnostic data set and the digital 3D representation;
   correlating the derived tooth information with individual teeth at least partly in accordance with the determined spatial correlation; and
   adding a representation of the derived tooth condition information to a digital dental chart.

2. The computer implemented method according to claim 1, wherein the diagnostic data set is extracted from another digital 3D representation of the patient's teeth that is different from the obtained digital 3D representation of the patient's teeth with which the spatial correlation of the part of the diagnostic data is determined.

3. The computer implemented method according to claim 1, wherein the diagnostic data is provided in form of two-dimensional images.

4. The computer implemented method according to claim 1, wherein the spatial correlation between the part of the diagnostic data of the diagnostic data set and the digital 3D representation is determined by aligning corresponding portions of the digital 3D representation and the part of the diagnostic data.

5. The computer implemented method according to claim 4, wherein aligning corresponding portions of the digital 3D representation and the part of the diagnostic data is based on one or more of fiducial markers, landmark, identification or aligning the surfaces using Iterative Closest Point algorithm.

6. The computer implemented method according to claim 1, further comprising segmenting individual teeth from the digital 3D representation, and wherein the tooth condition information is derived from variations in the diagnostic data over a portion of the segmented tooth of the digital 3D representation.

7. The computer implemented method according to claim 1, further comprising
   identifying individual teeth in the digital 3D representation; and
   correlating the derived tooth information with the individual teeth comprises determining a location of the tooth condition on the identified individual teeth.

8. The computer implemented method according to claim 1, wherein the tooth condition information further comprises the location of the condition on the identified tooth.

9. The computer implemented method according to claim 1, wherein
   deriving tooth condition information comprises deriving tooth condition information about specific locations of the one or more teeth from the diagnostic data; and
   correlating the derived tooth information comprises correlating the derived tooth information with the specific locations of the individual teeth.

10. The computer implemented method according to claim 1, further comprising
    obtaining the digital dental chart comprising regions representing surfaces of the patient's teeth; and
    correlating the individual teeth with the corresponding regions of the digital dental chart.

11. The computer implemented method according to claim 1, wherein adding the representation of the derived tooth condition information to a digital dental chart comprising mapping the representation of the derived tooth condition information about specific locations to corresponding region or regions of the digital dental chart.

12. The computer implemented method according to claim 1, wherein the obtained digital 3D representation of the patient's teeth with which the spatial correlation of the part of the diagnostic data is determined comprises at least another part of the diagnostic data.

13. The computer implemented method according to claim 1, wherein the diagnostic data comprises data selected from the group consisting of texture data, fluorescence data, Infrared data, X-ray data, optical coherence tomography data, ultrasound data, laser speckle images, or data representing the occlusal contact between antagonist teeth.

14. The computer implemented method according to claim 1, wherein the derived tooth condition information relates to information selected from the group consisting of tooth shade, tooth wear caries, presence of cariogenic bacteria, presence of fillings from previous dental work, acid erosion, damages, bruxism induced damages, tooth arrangement, malocclusion, or gingiva retraction.

15. The computer implemented method according to claim 1, wherein the obtained digital 3D representation comprises shape data for the teeth and another digital 3D representation comprises the diagnostic data; and the method further comprises determining the spatial correlation between the obtained digital 3D representation and another digital 3D representations.

16. The computer implemented method according to claim 15, further comprising forming a digital 3D representation comprising both the shape data of the obtained digital 3D representation and the diagnostic; data of another digital 3D representation.

17. The computer implemented method according to claim 1, wherein the regions of the teeth on the digital dental chart are based on the corresponding surfaces of the teeth of the digital 3D representation such that the regions of the dental chart are shaped and/or colored and/or arranged according to the patient's teeth.

18. The computer implemented method according to claim 1, wherein the correlation is expressed as a transformation configured to bring the digital 3D representation and the diagnostic data into a common coordinate system with a correct relative arrangement.

19. A non-transitory computer readable medium encoded with program code for populating a digital dental chart with deriving tooth condition information for a patient's teeth when said program code are executed on a data processing system, wherein said method comprises:
  obtaining a digital three dimensional (3D) representation of the patient's teeth;
  obtaining diagnostic data for one or more of the teeth, wherein at least a part of the diagnostic data is comprised in a diagnostic data set obtained in addition to the digital 3D representation of the patient's teeth;
  deriving tooth condition information from the diagnostic data;
  determining a spatial correlation between the part of the diagnostic data of the diagnostic data set and the digital 3D representation;
  correlating the derived tooth information with the individual teeth at least partly in accordance with the determined spatial correlation; and
  adding a representation of the derived tooth condition information to a digital dental chart.

20. The non-transitory computer readable medium according to claim 19, wherein
  the diagnostic data set is extracted from another digital 3D representation of the patient's teeth that is different from the obtained digital 3D representation of the patient's teeth with which the spatial correlation of the part of the diagnostic data is determined; and/or
  the diagnostic data is provided in form of two-dimensional images.

* * * * *